United States Patent [19]

Stiehl et al.

[11] Patent Number: 5,078,698
[45] Date of Patent: Jan. 7, 1992

[54] AXIAL EJECT HYPODERMIC SYRINGE HOLDER

[75] Inventors: Mark A. Stiehl; Eugene Sisto, both of Rochester, N.Y.

[73] Assignee: Sterling Drug Inc., New York, N.Y.

[21] Appl. No.: 657,026

[22] Filed: Feb. 19, 1991

[51] Int. Cl.$^5$ .............................................. A61M 5/00
[52] U.S. Cl. .................................................... 604/235
[58] Field of Search ................ 604/232, 235, 187, 218

[56] References Cited

U.S. PATENT DOCUMENTS

| | | | |
|---|---|---|---|
| 1,685,984 | 10/1928 | Cournand et al. | 604/235 |
| 2,392,196 | 1/1946 | Smith | 604/235 X |
| 3,144,178 | 8/1964 | Sarnoff. | |
| 3,348,545 | 10/1967 | Sarnoff et al. | 604/235 |
| 3,744,493 | 7/1973 | Booher et al. | 604/235 X |
| 4,585,445 | 4/1986 | Hodtke. | |
| 4,909,791 | 3/1990 | Norelli. | |
| 4,931,040 | 6/1990 | Haber et al. | |

Primary Examiner—John D. Yasko
Attorney, Agent, or Firm—William J. Davis

[57] ABSTRACT

A hypodermic syringe holder adapted to receive a disposable carpule and eject it in an axial direction includes a pair of pivotable jaws disposed on pivots on opposite sides of the body of the holder and a sleeve element for opening and closing the jaws slidably disposed around the body of the holder. In the downward position, the sleeve element closes the jaws around the carpule and in the upward position, the sleeve opens the jaws, permitting the carpule to be safely and consistently ejected form the holder in an axial direction.

7 Claims, 6 Drawing Sheets

FIG. 12
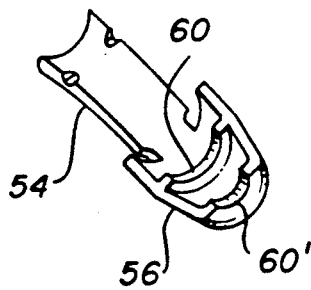
FIG. 13
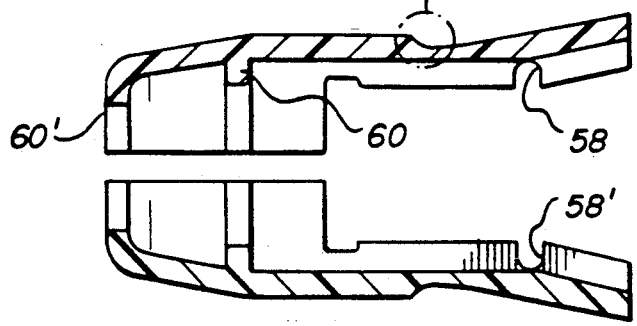
FIG. 13A
FIG. 14
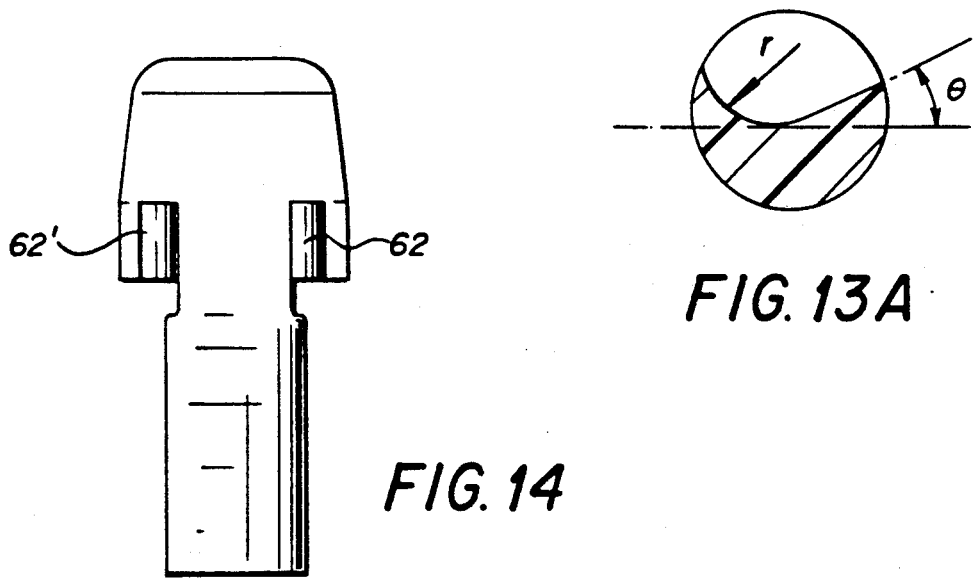

AXIAL EJECT HYPODERMIC SYRINGE HOLDER

FIELD OF THE INVENTION

This invention relates to hypodermic syringe holders for use in combination with disposable medicament-containing carpules.

BACKGROUND OF THE INVENTION

Reusable hypodermic syringe holders for use in conjunction with disposable pre-filled syringes, commonly referred to as carpules, containing fluid medication are well know in the art. One such holder which has achieved widespread commercial acceptance is described by F. B. Hadtke in U.S. Pat. No. 4,585,445. Another is described in commonly-owned U.S. patent application Ser. No. 609,963 filed Nov. 6, 1990 entitled Snap Together Hypodermic Syringe Holder. Such devices hold the carpule in place and facilitate the dispensing of the fluid medication from the carpule. The syringe holders permit disposal of the carpules without the need to handle the carpules themselves.

Nevertheless, medical workers are especially susceptible to accidental and potentially infectious needle strikes due to careless handling or disposing of the syringe after use. The consequences of coming into contact with various infectious diseases such as hepatitis or AIDS can be particularly severe.

The syringe holder described in U.S. Pat. No. 4,585,445 permits the carpule to be ejected from the side of the syringe holder. A problem with this and other syringe holders of the side eject type is that the ejected carpule does not follow a consistent repeatable trajectory. This can result in the ejected carpule falling outside the appropriate disposal containers provided for them. This increases the risk of accidental needle sticks. Furthermore, there is the potential for broken glass if the ejected carpule does not fall into the disposal container for which it is intended.

SUMMARY OF THE INVENTION

We have discovered a hypodermic syringe holder which minimizes the problems, e.g., accidental needle sticks and the potential for broken glass, associated with the prior art syringe holders of the side eject type.

More specifically, in accordance with the present invention, there is provided a hypodermic syringe holder adapted to receive a disposable carpule and eject it in an axial direction.

The holder includes a cylindrical hollow body, shaped to receive a carpule, the body comprising a head portion on the upper end thereof; an axially movable clamping element, rotatable about its longitudinal axis within the head portion of the body and engageable with an associated carpule to securely immobilize the carpule within the body of the syringe holder, the clamping element having a bore therethrough and comprising a handle portion and a barrel portion sized to rotate and translate within the head portion; a plunger element having a rod portion having on its lower end a piston engaging means, the rod portion and piston engaging means being axially and slidably receivable within the bore of the clamping element; a pair of pivotable jaws disposed on pivots on opposite sides of the body; and a sleeve element for opening and closing the jaws slidably disposed around the body of the holder. The sleeve element is slidable between a downward position and an upward position, such that the sleeve in the downward position closes the jaws around the carpule and in the upward position opens the jaws, permitting the carpule to be ejected from the holder in an axial direction.

It is an advantageous feature of this invention that there is provided a syringe holder assembly which facilitates the ejection of a carpule from the holder in an axial direction.

It is another advantageous feature of this invention that there is provided a syringe holder having pivotable jaws which can be opened widely and closed by sliding the sleeve element a small amount due to a camming actuation.

Yet another advantageous feature of this invention is that there is provided a syringe holder which can be easily assembled and readily operated.

Other advantages will become readily apparent upon reference to the following description of the preferred embodiments when read in light of the accompanying drawings.

BRIEF DESCRIPTION OF THE DRAWINGS

FIGS. 12, 13 and 14 are perspective, side cross-sectional and side elevational views, respectively, of the jaws.

DESCRIPTION OF THE PREFERRED EMBODIMENTS

While this invention is described hereinafter particularly with respect to a hypodermic syringe holder for use in conjunction with a disposable carpule, it also finds utility in other holders adapted to dispense a fluid from a disposable cartridge.

As used herein, the term "axial" is intended to make reference to a direction along the longitudinal axis of the syringe holder. The terms "lower" and "downward" are intended to make reference to the needle end of the syringe holder and associated parts. Conversely, the terms "upper" and "upward" are intended to make reference to the head (plunger) end of the holder.

Figure 1:
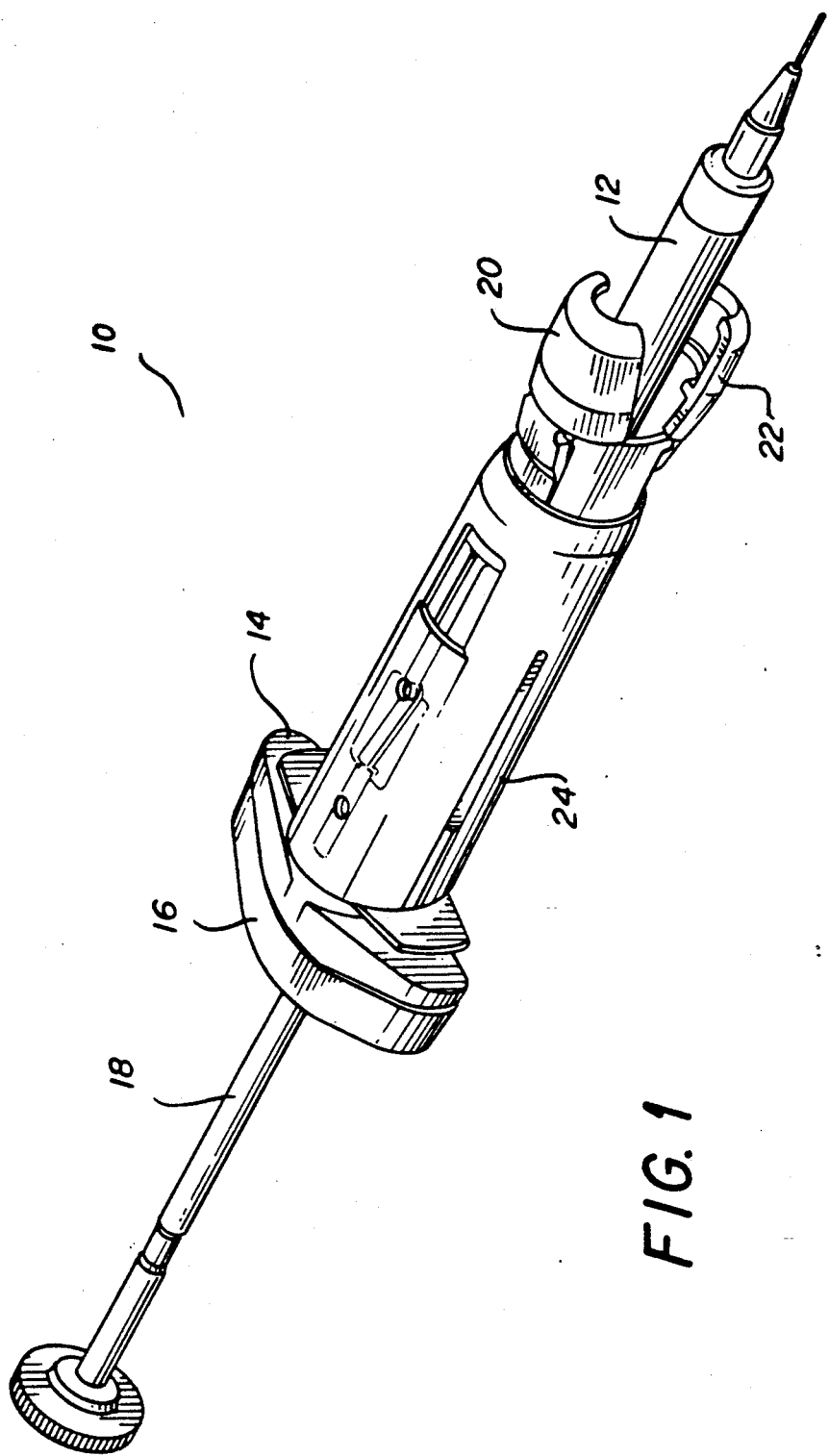
FIG. 1 is a perspective view of a preferred embodiment of the fully assembled syringe holder of the invention. The body, clamping element, plunger element, jaws and sleeve element of the holder are shown.

Referring to FIG. 1, the axial eject syringe holder of the invention, represented by 10, is intended for use in combination with conventional medicament containing carpules 12, which are closed at the upper end with a flexible piston slidable within the bore of the carpule and closed at the lower necked-down end by a rubber diaphragm secured to the carpule by a crimped on metal collar. The necked down end is conventionally fitted with a needle/needle hub unit and a needle sheath. A typical such carpule/needle assembly is sold commercially by Winthrop Pharmaceuticals under the trade name CARPUJECT™.

In preferred embodiments, the syringe holder comprises a total of six elements, namely, body 14, clamping element 16, plunger element 18, pivotable jaws 20 and 22, and sleeve element 24.

Figure 2:
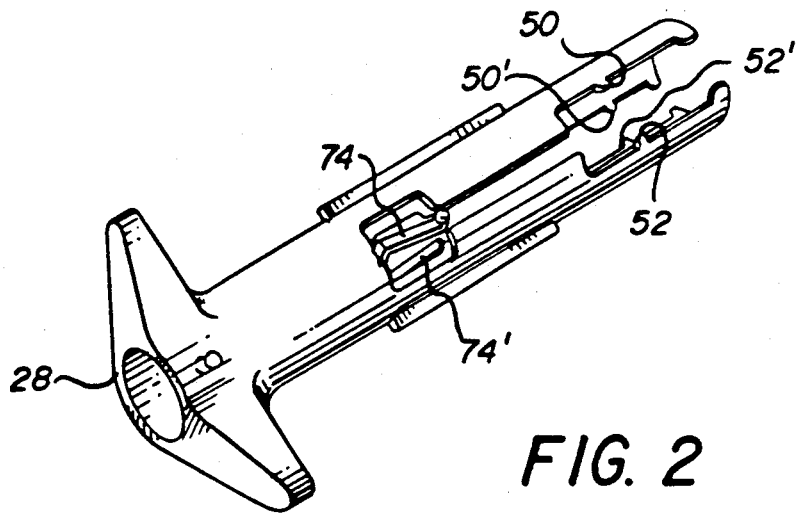
FIGS. 2, 3 and 4 are a perspective two side elevational views, respectively, of the body element.
Figure 3:
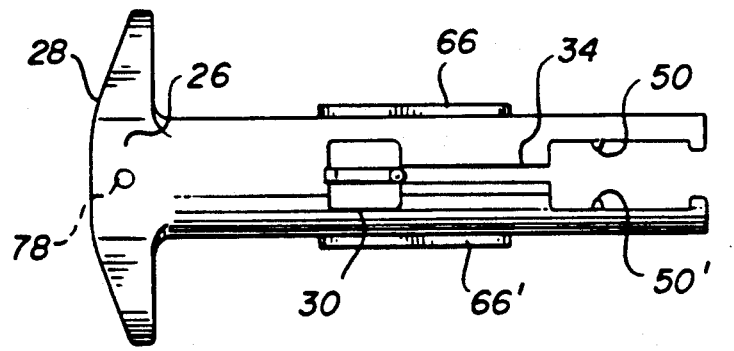
Figure 4:
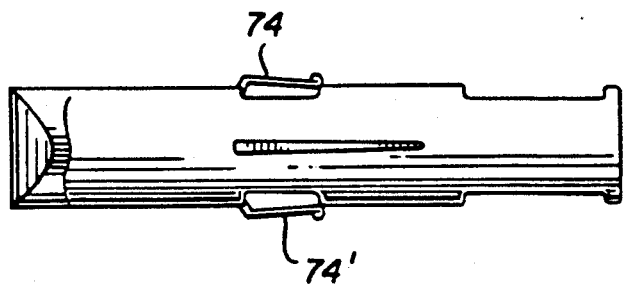

The body of the syringe holder, shown in FIGS. 2-4, is hollow and generally cylindrical in shape enabling it to receive a carpule. With reference to FIG. 3, the body comprises head portion 26 on the upper end thereof for receiving the clamping element. Finger gripping means 28 are provided for ease of manipulations. Preferably, the body can be sized to accept carpules having different sizes. Optional windows 30 and 30', and axial slots 34 and 34', can be provided within the body to facilitate injection molding of the part.

Figure 5:
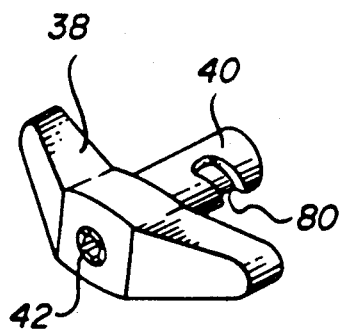
FIGS. 5, 6, 7 and 8 are perspective, side elevational, side cross-sectional and top end views, respectively, of the clamping element.
Figure 6:
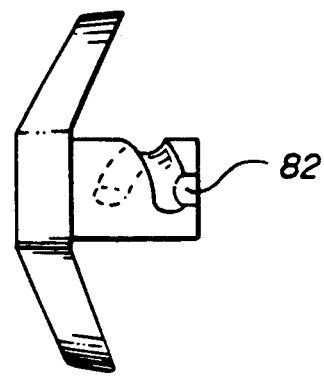
Figure 7:
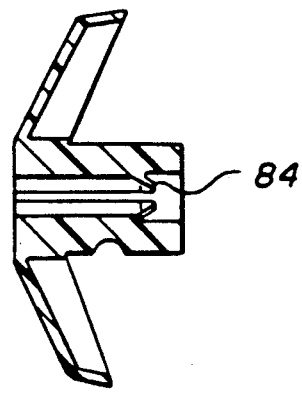
Figure 8:
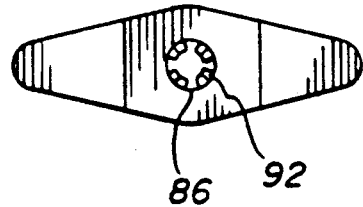

The clamping element, illustrated in FIGS. 5-8, is axially movable and rotatable about its longitudinal axis within the head portion of the body and is engageable with an associated carpule to securely immobilize the carpule within the body of the syringe holder. With reference to FIG. 5, the clamping element comprises handle portion 38 and barrel portion 40 sized to rotate and translate within the head portion of the body. The clamping element has a bore 42 therethrough sized to slidably receive at least the shaft of the plunger element.

Figure 9:
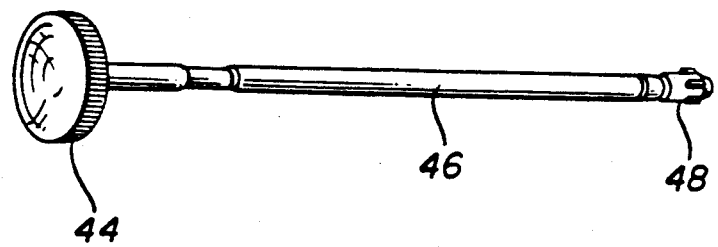
FIGS. 9, 10 and 11 are perspective, side elevational and bottom end views, respectively, of the plunger element.
Figure 10:
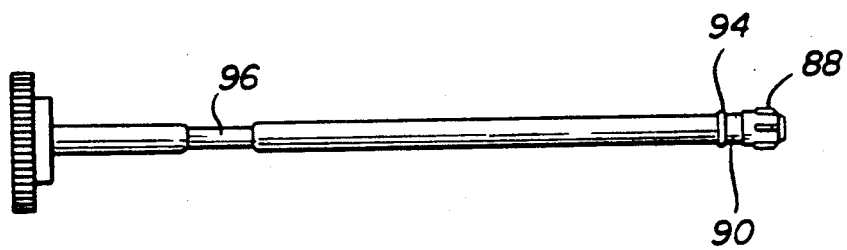
Figure 11:
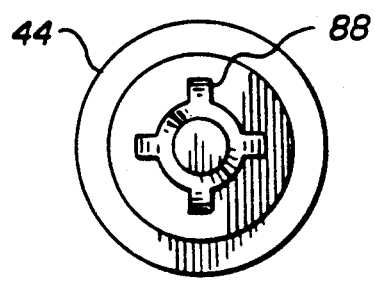

The plunger element, depicted in FIGS. 9-11, contains actuation button 44 on its upward end and rod portion 46 having on its lower end piston engaging means 48. The rod portion and piston engaging means are axially and slidable receivable within the bore of the clamping element. The piston engaging means is depicted as a threaded bore which can matably receive a screw-threaded post on the carpule piston. While such means is preferred, other piston engaging means, e.g. retractable claws, hooks, harpoons, etc., are know in the art and can serve the purpose as well.

An important feature of this invention is the pair of pivotable jaws, 20, 22' (FIG. 1), disposed on pivot pairs 50, 50', 52 and 52', (FIG. 2) located on opposite sides of the body. The jaws are illustrated in more detail in FIGS. 12-14.

Figure 15:
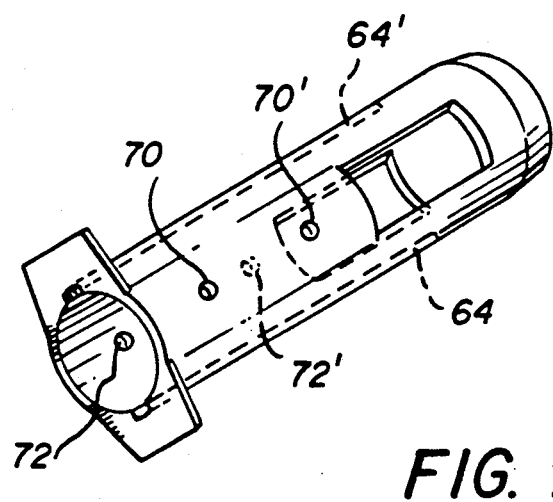
FIGS. 15, 16 and 17 are a perspective and two-side elevational views, respectively, of the sleeve element in a preferred embodiment of the syringe holder of the invention.
Figure 16:
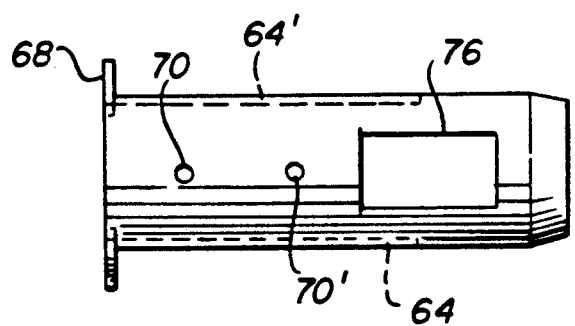
Figure 17:
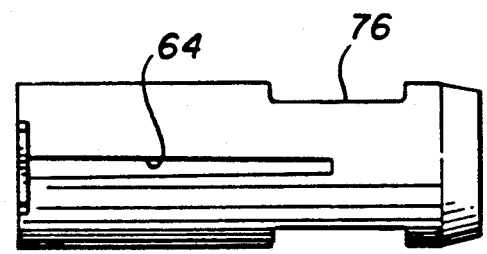

Another important feature of this invention is the sleeve element shown in FIGS. 15-17, for opening and closing the jaws, slidably disposed around the body of the holder. The sleeve element is slidable between a downward position and an upward position. In the downward position, the sleeve element closes the jaws around the carpule. In the upward position, the sleeve element opens the jaws, permitting the carpule to be ejected from the syringe holder in an axial direction.

With reference to FIGS. 12-14, each jaw contains wing portion 54 and cone portion 56. The outer surface of the wing portion defines a cam path. The lower surface of the sleeve element defines the cam path follower. We have found that radius r and wing angle $\phi$ depicted in FIG. 13 are important design parameters in defining a functional cam path. For a holder designed for use with conventional carpules, it is highly desirable that radius r satisfy the relation $0.10 \text{ cm} < r < 0.25 \text{ cm}$, and that wing angle $\phi$ satisfy the relation $10° < \phi < 15°$. This advantageously insures that a large jaw actuation results from a small sleeve displacement. The large jaw opening resulting from the camming actuation minimizes the potential for the carpule to strike the jaws while exiting from the holder. As is apparent, no camming action occurs while the jaws are opened. Each jaw contains a pair of recesses 58 and 58' preferably radial in shape, to accept the pivots. While the Figures depict the pivots provided on the body, it will be readily apparent to one skilled in art that the pivots can be provided on the jaws and mating recesses on the body. The cone portion of the jaws preferably can be provided with one or more arcuately shaped ribs 60 and 60'. Such ribs add strength to the jaws and provide stability to the carpule by aiding the retention and immobilization of the carpule. The outer surface of the cone portion of the jaws can contain raised pressure pads 62 and 62' which hold the jaws closed in the downward position during use of the syringe holder by accepting the force from the sleeve element.

Turning to FIGS. 15-17, the sleeve element preferably is provided with a pair of axial slots 64 and 64' on opposite sides which function to align and stabilize the sleeve in conjunction with mating axial ribs 66 and 66' (FIG. 3) preferably provided on the body of the holder. The sleeve can be provided with flanges 68 which can be gripped by the fingers of the dispenser to open the jaws, thus facilitating the dispensing of the contents of the carpule and the actuation of the jaws via a one hand operation. The sleeve element can further comprise one or more sets of holes 70, 70', 72 and 72' spaced apart by an amount about equal to the longitudinal displacement of the sleeve between the downward and upward positions. Such holes function as detents in conjunction with mating projections, i.e., snap tabs 74 and 74' (FIG. 4) on the body to help hold the sleeve element and body together. The sleeve can also contain windows 76 and 76' on opposite sides which allow the wings of the jaws to wing up when the jaws are in the closed position. The upper end surface of the wing portion of the jaw contacts the upper surface of the window as the sleeve is pushed downward, stopping the sleeve in its downmost position. The lower inside surface of the sleeve element preferably is provided with a slight taper which facilitates the functioning of the lower end of the sleeve as a cam path follower. The lower end of the sleeve can be provided with a taper on the outside surface.

In a particularly preferred embodiment of the invention, the head portion of the body contains on its inside surface projecting lug 78 (FIG. 3). The lug is preferably hemispherical. In this embodiment, the clamping element comprises helical groove 80 (FIG. 5) on the outer surface of the barrel portion and ramp means 82 (FIG. 6) connecting the helical groove with the lower surface of the clamping element, so that the helical groove is slidably accessible to the lug through the ramp means and engageable with the lug.

In preferred embodiments of the invention, the clamping element can be provided with fingers 84 (FIG. 7) and grooves 86 (FIG. 8) on the inside diameter of the bore, and the head portion of the rod can be provided with fins 88 and the lower power of the rod with undercut means 90 (FIG. 10). When inserted through the bore, the fins travel through the grooves and the head of the rod is capable of flexing the fingers. The fingers are engageable with the undercut means to capture the plunger element in the clamping element. Keying means 92 (FIG. 8) can be provided so that the fins align themselves with the grooves upon insertion of the head portion of the plunger element into the bore. The rod can be provided with radial ribs 94 and detent means 96 (FIG. 10) which retain the plunger rod in the upward position and facilitate carpule ejection.

As noted above, the various elements of the syringe holder of the invention can be readily assembled. For example, the plunger element can be inserted through the bore of the clamping element in an "insert only" manner. The resulting clamping element/plunger element subassembly can then be inserted into the head portion of the body. Thereafter, the jaws can be positioned on the pivots in the closed position and then the sleeve can be slid over both the jaws and the body.

The various elements of the syringe holder described herein can be made of any suitable material including metals or plastics. However, they are well adapted to fabrication of plastic. In particular, the various elements can be fabricated of rigid plastic using known precision injection molding techniques. Suitable plastics include high density polypropylene, polystyrene, polycarbonates, ABS (clear or opaque), nylon, acetals such DELRIN or polyethylene. It is particularly desirable that the plastic selected be substantially resistant to deformation at sterilization temperatures when the holder is intended for use in a high temperature, sterilization process, e.g., in an autoclave.

In use, the clamping element is fully retracted by turning one half turn in the disengaging direction. The sleeve is pulled to its upward position, opening the jaws. The upper end of the carpule cartridge unit can then be inserted through the open jaws into the body of the syringe holder. The jaws close by sliding the sleeve element downward and then the clamping element is rotated to lock the carpule in place. The plunger rod is rotated to engage the carpule. The injection can then proceed in the normal manner by pushing the actuation button, thereby sliding the plunger element forward and dispensing the contents of the carpule. To disengage the carpule, the plunger rod is unscrewed. Then the unit is placed over an appropriate disposal container and the sleeve is pulled into its upward position opening the jaws to expel the carpule. Accordingly, the carpule can be ejected from the syringe holder safely and consistently in an axial direction.

In an alternative embodiment, it is contemplated that the jaws can be spring loadable. For example, spring means can be attached to each jaw which function to force the jaw open when the jaw is not constrained by the sleeve. It is specifically contemplated that the spring means can comprise an appropriately biased flat rectangular wire or steel band. One end of the band can be inserted into a rectangular cavity provided in the jaw, the jaw preferably containing spring retention means. The opposite end of the band can float between the sleeve and the body. An advantage of such a design is that the sleeve is not required to function as a camming actuator.

The invention has been described in detail with particular reference to preferred embodiments thereof, but it will be understood that variations and modifications can be effected within the spirit and scope of the invention.

What is claimed is:

1. A hypodermic syringe holder adapted to receive a disposable carpule and eject it in an axial direction comprising:
    a generally cylindrical hollow body shaped to receive a carpule, said body comprising a head portion on the upper end thereof:
    an axially movable clamping element rotatable about its longitudinal axis within the head portion of said body and engageable with an associated carpule to securely immobilize the carpule within the body of the syringe holder, said clamping element having a bore therethrough and comprising a handle portion and a barrel portion sized to rotate and translate within said head portion of said body:
    a plunger element having a rod portion which bears on its lower end a piston engaging means, said rod portion being axially and slidably receivable within the bore of said clamping element:
    a pair of pivotable jaws disposed on pivots on opposite sides of said body; and
    a sleeve element for opening and closing the jaws slidably disposed around the body of the holder and slidable between a downward position and an upward position, such that said sleeve element in the downward position closes the jaws around the carpule and in the upward position opens the jaws, thereby permitting the carpule to be received within, and then later ejected from, the holder in an axial direction.

2. The syringe holder of claim 1 wherein each said jaw contains a wing portion having an outer surface which defines a cam path and the lower surface of said sleeve defines a cam path follower.

3. The syringe holder of claim 1 wherein said sleeve contains window means which accept the wing portions of said jaws when said jaws are in the closed position.

4. The syringe holder of claim 1 wherein said sleeve contains an axial slot and said body contains an axial rib which mates with said slot.

5. The syringe holder of claim 1 wherein said sleeve contains a set of holes and said body contains a set of mating projections, each set of said holes and projections being longitudinally displaced by an amount about equal to the longitudinal displacement of the sleeve between said downward and upward positions.

6. The syringe holder of claim 1 wherein said head portion of said body contains on its inside surface a projecting lug and said clamping element further comprises a helical groove on the outer surface of said barrel portion and ramp means connecting said helical groove with the lower surface of said clamping element, so that said helical groove is slidably accessible to the lug through the ramp means and engageable with the lug.

7. The syringe holder of claim 1, further including spring means which force said jaws open when said sleeve element is in the upward position.

* * * * *